(12) United States Patent
Baker et al.

(10) Patent No.: US 9,572,578 B2
(45) Date of Patent: Feb. 21, 2017

(54) SLITTED TISSUE FIXATION DEVICES AND ASSEMBLIES FOR DEPLOYING THE SAME

(71) Applicant: EndoGastric Solutions, Inc., Redmond, WA (US)

(72) Inventors: Steve G. Baker, Redwood, WA (US); Stefan J. M. Kraemer, Seattle, WA (US); Raymond Michael Wolniewicz, III, Redmond, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 0 days.

(21) Appl. No.: 15/152,337

(22) Filed: May 11, 2016

(65) Prior Publication Data

US 2016/0270787 A1 Sep. 22, 2016

Related U.S. Application Data

(60) Division of application No. 13/680,944, filed on Nov. 19, 2012, now Pat. No. 9,358,007, which is a
(Continued)

(51) Int. Cl.
*A61B 17/08* (2006.01)
*A61B 17/064* (2006.01)
(Continued)

(52) U.S. Cl.
CPC ............. *A61B 17/08* (2013.01); *A61B 17/064* (2013.01); *A61B 17/10* (2013.01);
(Continued)

(58) Field of Classification Search
CPC ..... A61B 17/08; A61B 17/10; A61B 17/0057; A61B 2017/00827; A61B 2017/00606; A61B 2017/00628; A61B 2017/00623; A61B 2017/0417; A61B 2017/0419; A61B 2017/0409
(Continued)

(56) References Cited

U.S. PATENT DOCUMENTS

| 2,753,870 | A | 7/1956 | Muffly |
| 3,875,928 | A | 4/1975 | Angelchik |

(Continued)

FOREIGN PATENT DOCUMENTS

| EP | 252607 A2 | 9/1992 |
| WO | 9922649 A2 | 5/1999 |

(Continued)

OTHER PUBLICATIONS

The gastroesophageal flap valve: in vitro and in vivo observations; Lucius D. Hill et al.; Gastrointestinal Endoscopy; vol. 44, No. 5, 1996; pp. 541-547; abstract.
(Continued)

*Primary Examiner* — Todd E Manahan
*Assistant Examiner* — Charles Wei
(74) *Attorney, Agent, or Firm* — Fulwider Patton LLP

(57) ABSTRACT

Tissue fasteners carried on a tissue piercing deployment wire fasten tissue layers of a mammalian body together include a first member, a second member, and a connecting member extending between the first and second members. One of the first and second members has a configuration alterable by a deployment wire to permit release of the fastener from the deployment wire after deployment and without causing excessive tissue trauma.

10 Claims, 11 Drawing Sheets

Related U.S. Application Data continuation of application No. 12/803,077, filed on Jun. 17, 2010, now Pat. No. 8,337,514, which is a continuation of application No. 11/043,903, filed on Jan. 25, 2005, now abandoned.

(51) Int. Cl.
*A61B 17/10* (2006.01)
*A61B 17/00* (2006.01)
*A61B 17/22* (2006.01)

(52) U.S. Cl.
CPC ........... *A61B 2017/00827* (2013.01); *A61B 2017/00862* (2013.01); *A61B 2017/0645* (2013.01); *A61B 2017/22044* (2013.01); *A61B 2090/037* (2016.02); *A61B 2090/3937* (2016.02)

(58) Field of Classification Search
USPC ....... 606/139, 142, 143, 151, 191, 215, 216, 606/232; 227/66, 67
See application file for complete search history.

(56) References Cited

U.S. PATENT DOCUMENTS

| | | |
|---|---|---|
| 4,006,747 A | 2/1977 | Kronenthal |
| 4,271,828 A | 6/1981 | Angelchik |
| 4,576,772 A | 3/1986 | Carpenter et al. |
| 4,595,007 A | 6/1986 | Mericle |
| 4,669,473 A | 6/1987 | Richards et al. |
| 4,696,300 A * | 9/1987 | Anderson ............ A61B 17/04 273/DIG. 5 |
| 4,846,836 A | 7/1989 | Reich |
| 4,895,148 A | 1/1990 | Bays et al. |
| 4,921,479 A | 5/1990 | Grayzel |
| 5,006,106 A | 4/1991 | Angelchik et al. |
| 5,041,129 A * | 8/1991 | Hayhurst ............ A61B 17/0401 606/139 |
| 5,080,543 A | 1/1992 | Murphy |
| 5,088,979 A | 2/1992 | Filipi et al. |
| 5,254,126 A | 10/1993 | Filipi et al. |
| 5,314,473 A | 5/1994 | Godin |
| 5,403,326 A | 4/1995 | Harrison et al. |
| 5,411,508 A | 5/1995 | Bessler et al. |
| 5,411,520 A | 5/1995 | Nash et al. |
| 5,549,621 A | 8/1996 | Bessler et al. |
| 5,549,631 A * | 8/1996 | Bonutti ............ A61B 17/0401 606/232 |
| 5,571,074 A | 11/1996 | Buckman et al. |
| 5,571,116 A | 11/1996 | Bolanos et al. |
| 5,626,614 A * | 5/1997 | Hart ................ A61B 17/0401 606/144 |
| 5,676,674 A | 10/1997 | Bolanos et al. |
| 5,713,903 A | 2/1998 | Sander et al. |
| 5,759,151 A | 6/1998 | Sturges |
| 5,810,882 A | 9/1998 | Bolduc et al. |
| 5,814,054 A | 9/1998 | Kortenbach et al. |
| 5,861,036 A | 1/1999 | Godin |
| 5,879,372 A | 3/1999 | Bartlett et al. |
| 5,887,594 A | 3/1999 | LoCicero |
| 5,897,562 A | 4/1999 | Bolanos et al. |
| 5,938,668 A | 8/1999 | Scirica et al. |
| 6,086,600 A | 7/2000 | Kortenbach |
| 6,098,629 A | 8/2000 | Johnson et al. |
| 6,113,609 A | 9/2000 | Adams |
| 6,113,611 A | 9/2000 | Allen et al. |
| 6,142,957 A | 11/2000 | Diamond et al. |
| 6,254,642 B1 | 7/2001 | Taylor |
| 6,264,700 B1 | 7/2001 | Kilcoyne et al. |
| 6,302,311 B1 | 10/2001 | Adams et al. |
| 6,302,917 B1 | 10/2001 | Dua et al. |
| 6,312,437 B1 | 11/2001 | Kortenbach |
| 6,315,789 B1 | 11/2001 | Cragg |
| 6,419,669 B1 | 7/2002 | Frazier et al. |
| 6,428,548 B1 | 8/2002 | Durgin et al. |
| 6,447,524 B1 | 9/2002 | Knodel et al. |
| 6,743,239 B1 | 6/2004 | Kuehn et al. |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,835,200 B2 | 12/2004 | Laufer et al. |
| 6,916,332 B2 | 7/2005 | Adams |
| 6,921,361 B2 | 7/2005 | Suzuki et al. |
| 7,022,118 B2 | 4/2006 | Ariura et al. |
| 7,037,344 B2 | 5/2006 | Kagan et al. |
| 7,074,229 B2 | 7/2006 | Adams et al. |
| 7,083,630 B2 | 8/2006 | DeVries et al. |
| 7,220,266 B2 | 5/2007 | Gambale |
| 7,347,863 B2 | 3/2008 | Rothe et al. |
| 7,618,426 B2 | 11/2009 | Ewers et al. |
| 7,632,287 B2 | 12/2009 | Baker et al. |
| 7,678,123 B2 | 3/2010 | Chanduszko |
| 7,713,277 B2 | 5/2010 | Laufer et al. |
| 7,776,057 B2 | 8/2010 | Laufer et al. |
| 7,850,704 B2 | 12/2010 | Burnett et al. |
| 7,857,184 B2 | 12/2010 | Viola |
| 7,857,823 B2 | 12/2010 | Laufer et al. |
| 7,866,526 B2 | 1/2011 | Green et al. |
| 7,942,887 B2 | 5/2011 | Kraemer et al. |
| 7,951,157 B2 | 5/2011 | Gambale |
| 7,954,687 B2 | 6/2011 | Zemlok et al. |
| 7,955,340 B2 | 6/2011 | Michlitsch et al. |
| 8,057,494 B2 | 11/2011 | Laufer et al. |
| 8,252,009 B2 | 8/2012 | Weller et al. |
| 8,277,468 B2 | 10/2012 | Laufer et al. |
| 8,308,765 B2 | 11/2012 | Saadat et al. |
| 8,343,175 B2 | 1/2013 | Ewers et al. |
| 8,574,243 B2 | 11/2013 | Saadat et al. |
| 2002/0022853 A1 | 2/2002 | Swanson et al. |
| 2002/0035370 A1 | 3/2002 | Kortenbach |
| 2002/0040226 A1 | 4/2002 | Laufer et al. |
| 2002/0055772 A1 | 5/2002 | McGuckin, Jr. et al. |
| 2002/0072761 A1 | 6/2002 | Abrams et al. |
| 2002/0078967 A1 | 6/2002 | Sixto, Jr. et al. |
| 2002/0082621 A1 | 6/2002 | Schurr et al. |
| 2002/0143349 A1 | 10/2002 | Gifford, III et al. |
| 2002/0183765 A1 | 12/2002 | Adams |
| 2002/0198541 A1 | 12/2002 | Smith et al. |
| 2003/0023230 A1 | 1/2003 | Lewis et al. |
| 2003/0055442 A1 | 3/2003 | Laufer et al. |
| 2003/0065359 A1 | 4/2003 | Weller et al. |
| 2003/0093117 A1 | 5/2003 | Saadat |
| 2003/0120289 A1 | 6/2003 | McGuckin, Jr. et al. |
| 2003/0120292 A1 | 6/2003 | Park et al. |
| 2003/0171760 A1 | 9/2003 | Gambale |
| 2003/0187465 A1 | 10/2003 | Bailly et al. |
| 2003/0191497 A1 | 10/2003 | Cope |
| 2003/0216613 A1 | 11/2003 | Suzuki et al. |
| 2003/0216754 A1 | 11/2003 | Kraemer et al. |
| 2003/0220657 A1 | 11/2003 | Adams |
| 2004/0044304 A1 | 3/2004 | Hill et al. |
| 2004/0044364 A1 | 3/2004 | DeVries et al. |
| 2004/0087976 A1 | 5/2004 | DeVries et al. |
| 2004/0093024 A1 | 5/2004 | Lousararian et al. |
| 2004/0116949 A1 | 6/2004 | Ewers et al. |
| 2004/0133236 A1 | 7/2004 | Chanduszko |
| 2004/0138529 A1 | 7/2004 | Wiltshire et al. |
| 2004/0147958 A1 | 7/2004 | Lam et al. |
| 2004/0148034 A1 | 7/2004 | Kagan et al. |
| 2004/0153102 A1 | 8/2004 | Therin et al. |
| 2004/0153103 A1 | 8/2004 | Schwartz et al. |
| 2004/0162568 A1 | 8/2004 | Saadat et al. |
| 2004/0215216 A1 | 10/2004 | Gannoe et al. |
| 2004/0236357 A1 | 11/2004 | Kraemer et al. |
| 2004/0243223 A1 | 12/2004 | Kraemer et al. |
| 2005/0004575 A1 | 1/2005 | Sgro et al. |
| 2005/0017781 A1 | 1/2005 | Honda |
| 2005/0043759 A1 | 2/2005 | Chanduszko |
| 2005/0075653 A1 | 4/2005 | Saadat et al. |
| 2005/0085829 A1 | 4/2005 | Kraemer et al. |
| 2005/0154405 A1 | 7/2005 | Kraemer et al. |
| 2005/0177176 A1 | 8/2005 | Gerbi et al. |

(56) References Cited

U.S. PATENT DOCUMENTS

| | | |
|---|---|---|
| 2005/0187565 A1 | 8/2005 | Baker et al. |
| 2005/0203547 A1 | 9/2005 | Weller et al. |
| 2005/0216040 A1 | 9/2005 | Gertner et al. |
| 2005/0228413 A1 | 10/2005 | Binmoeller et al. |
| 2005/0247320 A1 | 11/2005 | Stack et al. |
| 2005/0251176 A1 | 11/2005 | Swanstrom et al. |
| 2006/0009789 A1 | 1/2006 | Gambale |
| 2006/0190018 A1 | 8/2006 | Baker et al. |
| 2006/0253130 A1 | 11/2006 | Wolniewicz |
| 2006/0253142 A1 | 11/2006 | Bjerken |
| 2007/0021756 A1 | 1/2007 | Kortenbach |
| 2007/0021760 A1 | 1/2007 | Kelleher |
| 2007/0112363 A1 | 5/2007 | Adams |
| 2007/0129738 A1 | 6/2007 | Kraemer et al. |
| 2007/0191870 A1 | 8/2007 | Baker et al. |
| 2007/0191871 A1 | 8/2007 | Baker et al. |
| 2007/0219566 A1 | 9/2007 | Gambale |
| 2007/0276409 A1 | 11/2007 | Ortiz et al. |
| 2008/0015618 A1 | 1/2008 | Sonnenschein et al. |
| 2008/0287966 A1 | 11/2008 | Kraemer et al. |
| 2008/0294179 A1 | 11/2008 | Balbierz et al. |
| 2009/0177214 A1 | 7/2009 | Adams |
| 2009/0198254 A1 | 8/2009 | Laufer et al. |
| 2009/0236388 A1 | 9/2009 | Cole et al. |
| 2010/0241139 A1 | 9/2010 | Harshman |
| 2011/0196391 A1 | 8/2011 | Forsell |
| 2011/0213390 A1 | 9/2011 | Kraemer et al. |

FOREIGN PATENT DOCUMENTS

| | | |
|---|---|---|
| WO | 9960931 A1 | 12/1999 |
| WO | 0053102 A1 | 9/2000 |
| WO | 0078227 A1 | 12/2000 |
| WO | 0132084 A1 | 5/2001 |
| WO | 0135834 A1 | 5/2001 |
| WO | 0164964 A1 | 9/2001 |
| WO | 0167964 A2 | 9/2001 |
| WO | 0185034 A1 | 11/2001 |
| WO | 0189391 A1 | 11/2001 |
| WO | 0224058 A2 | 3/2002 |
| WO | 0224080 A2 | 3/2002 |
| WO | 0228289 A1 | 4/2002 |
| WO | 02082621 A1 | 10/2002 |
| WO | 02096327 A2 | 12/2002 |
| WO | 03061480 A1 | 7/2003 |
| WO | 03099140 A1 | 12/2003 |
| WO | 2004019787 A2 | 3/2004 |
| WO | 2004019788 A2 | 3/2004 |
| WO | 2004049982 A2 | 6/2004 |
| WO | 2004069055 A2 | 8/2004 |
| WO | 2005065412 A2 | 7/2005 |
| WO | 2005081817 A2 | 9/2005 |
| WO | 2006023764 A2 | 3/2006 |
| WO | 2006034484 A2 | 3/2006 |
| WO | 2006081368 A2 | 8/2006 |
| WO | 2007002817 A2 | 1/2007 |
| WO | 2007064713 A2 | 6/2007 |
| WO | 2010087756 A1 | 8/2010 |

OTHER PUBLICATIONS

Reappraisal of the flap valve mechanism in the gastroesophageal junction: A study of a new valvuloplasty procedure in cadavers; KjellB.A. Thor et al.; Acta Chir Scand 153:25-28, 1987; abstract.
The Plicator Procedure; 1 page; abstract.
Chuttani, MD. et al., "A novel endoscopic full-thickness plicator for treatment of GERD: an animal model study". Gastrointestinal Endoscopy, vol. 56, No. 1, 2002, pp. 116-122; abstract.
Jobe, et al., "Endoscopic Appraisal of the Gastroesophageal Valve After Antireflux Surgery", American Journal of Gastroenterology, ISSN 0002-9270; abstract.
International Search Report for PCT/US2012/054328.

* cited by examiner

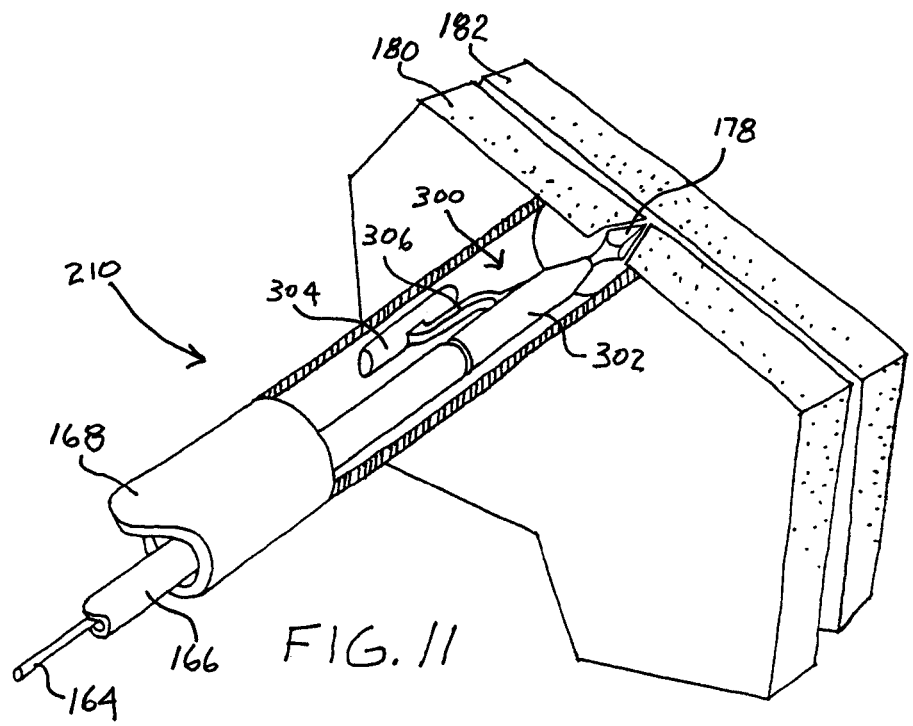
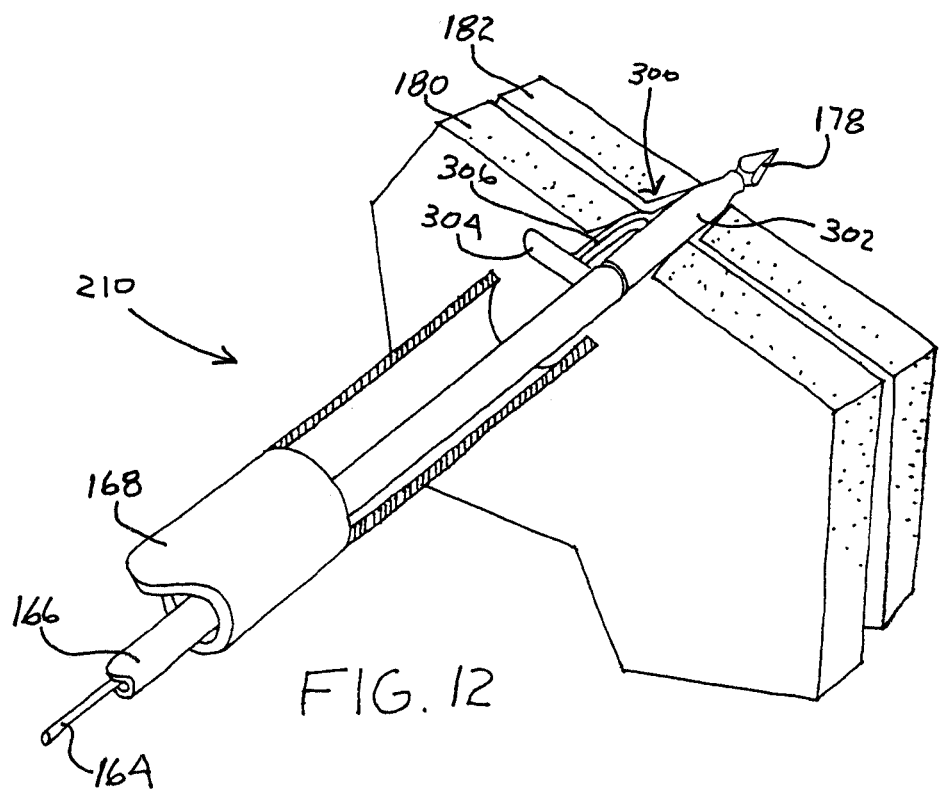

SLITTED TISSUE FIXATION DEVICES AND ASSEMBLIES FOR DEPLOYING THE SAME

This application is a division of U.S. application Ser. No. 13/680,944, filed Nov. 19, 2012, which is a continuation of U.S. application Ser. No. 12/803,077, filed Jun. 17, 2010, now U.S. Pat. No. 8,337,514 issued Dec. 25, 2012, which is a continuation of U.S. application Ser. No. 11/043,903, filed Jan. 25, 2005, now abandoned, the entire disclosures of which are hereby incorporated by reference for all purposes.

FIELD OF THE INVENTION

The present invention generally relates to tissue fixation devices, and more particularly to devices for treating gastroesophageal reflux disease using the same. The present invention more particularly relates to such tissue fixation devices which may be used in surgical environments and which are self-deploying.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

A principal reason for regurgitation associated with GERD is the mechanical failure of a deteriorated gastroesophageal flap to close and seal against high pressure in the stomach. Due to reasons including lifestyle, a Grade I normal gastroesophageal flap may deteriorate into a malfunctioning Grade III or absent valve Grade IV gastroesophageal flap. With a deteriorated gastroesophageal flap, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus) results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a precancerous lining (called Barrett's Esophagus) in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury.

GERD never improves without intervention. Life style changes combined with both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10% of the GERD cases. The esophageal epithelium changes into tissue that tends to become cancerous from repeated acid washing despite the medication.

Several open laparotomy and laproscopic surgical procedures are available for treating GERD. One surgical approach is the Nissen fundoplication. The Nissen approach typically involves a 360-degree wrap of the fundus around the gastroesophageal junction. The procedure has a high incidence of postoperative complications. The Nissen approach creates a 360-degree moveable flap without a fixed portion. Hence, Nissen does not restore the normal movable flap. The patient cannot burp because the fundus was used to make the repair, and may frequently experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore the normal movable flap. None of these procedures fully restores the normal anatomical anatomy or produces a normally functioning gastroesophageal junction. Another surgical approach is the Hill repair. In the Hill repair, the gastroesophageal junction is anchored to the posterior abdominal areas, and a 180-degree valve is created by a system of sutures. The Hill procedure restores the moveable flap, the cardiac notch and the Angle of His. However, all of these surgical procedures are very invasive, regardless of whether done as a laproscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device on one arm. The arm then pulls on the engaged portion to create a fold of tissue or radial plication at the gastroesophageal junction. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak, in part due to the fact, that the esophagus is not covered by serosa, a layer of very sturdy, yet very thin tissue, covering and stabilizing all intraabdominal organs, similar like a fascia covering and stabilizing muscle. Involvement of esophageal tissue in the repair of a gastroesophageal flap valve poses unnecessary risks to the patient, such as an increased risk of fistulas between the esophagus and the stomach.

A new and improved apparatus and method for restoration of a gastroesophageal flap valve is fully disclosed in copending U.S. application Ser. No. 10/150,740, now U.S. Pat. No. 6,790,214, filed May 17, 2002, for TRANSORAL ENDOSCOPIC GASTROESOPHAGEAL FLAP VALVE RESTORATION DEVICE, ASSEMBLY, SYSTEM AND METHOD, is assigned to the assignee of this invention, and is incorporated herein by reference. That apparatus and method provides a transoral endoscopic gastroesophageal flap valve restoration. A longitudinal member arranged for transoral placement into a stomach carries a tissue shaper that non-invasively grips and shapes stomach tissue. A tissue fixation device is then deployed to maintain the shaped stomach tissue in a shape approximating a gastroesophageal flap.

Whenever tissue is to be maintained in a shape as, for example, in the improved assembly last mentioned above, it is necessary to fasten at least two layers of tissue together. In applications such as gastroesophageal flap valve restoration, there is very limited room to maneuver a fastener deployment device. For example, this and other medical fastening applications provide confined working channels and spaces and often must be fed through an endoscope to permit visualization or other small lumen guide catheters to the place where the fasteners are to be deployed. To make matters worse, multiple fasteners may also be required. Hence, with current fasteners and deployment arrangements, it is often difficult to direct a single fastener to its intended location, let alone a number of such fasteners.

Once the fastening site is located, the fasteners employed must be truly able to securely maintain the tissue. Still further, the fastener must be readily deployable. Also, quite obviously, the fasteners are preferably deployable in the tissue in a manner, which does not unduly traumatize the tissue.

SUMMARY

The invention provides a fastener for use in a mammalian body. The fastener comprises a first member and a second member, wherein the first and second members have first and second ends. The fastener further comprises a connecting member fixed to each of the first and second members intermediate the first and second ends and extending between the first and second members. The first and second members are separated by the connecting member and one of the first and second members has a through channel along the axis arranged to be slidingly received on a tissue piercing deployment wire, and a slit extending between the first and second ends and communicating with the through channel.

The slit is substantially parallel to the through channel. The slit may include an elongated slot portion dimensioned to receive the tissue piercing deployment wire. The slit further has a width less than the diameter of the through channel.

The invention further provides a fastener assembly for use in a mammalian body, comprising a fastener including a first member and a second member. The first and second members have first and second ends. The fastener further comprises a connecting member fixed to each of the first and second members intermediate the first and second ends and extending between the first and second members. The first and second members are separated by the connecting member, and one of the first and second members has a longitudinal axis, a through channel along the axis, and a slit between the first and second ends and communicating with the through channel. The assembly further comprises a deployment wire arranged to be slidingly received by the through channel of the one of the first and second members and to pierce into the tissue. The deployment wire is arranged to be received by the slit to enable early deployment of the one of the first and second members and reduced tissue compression. The assembly further comprises a pusher that pushes the one of first and second members into the tissue while on the deployment wire.

The invention further comprises a fastener assembly for use in a mammalian body compromising a fastener including a first member, and a second member, wherein the first and second members have first and second ends. The fastener further comprises a connecting member fixed to each of the first and second members intermediate the first and second ends and extends between and separates the first and second members. The one of the first and second members has a longitudinal axis, a through channel along the axis, and a slit extending between the first and second ends and communicating with the through channel. The assembly further comprises a deployment wire arranged to be slidingly received by the through channel of the one of the first and second members and has a pointed tip to pierce into tissue, the pointed tip having a cross-sectional dimension equal to or greater than the cross-sectional dimension of the through channel. The assembly further comprises a pusher that pushes the one of the first and second members into the tissue while on the deployment wire.

The invention still further provides a fastener assembly for use in a mammalian body, comprising a deployment wire having an end arranged to pierce into tissue to be fastened, a fastener including a member having a through channel dimensioned to be slidingly received on the deployment wire, and a pusher that pushes the fastener into the tissue while on the deployment wire. The pusher is tubular having a distal end, a sidewall, a lumen, and an opening in the sidewall communicating with the lumen. The pusher is carried on the deployment wire with the deployment wire extending through the sidewall opening, into the lumen, and beyond the distal end of the pusher. The fastener member is carried on the deployment wire between the deployment wire end and the distal end of the pusher arranged to pierce into the tissue upon being pushed by the pusher.

The invention further provides a fastener for use in a mammalian body comprising a first member, a second member, the first and second members having first and second ends, and a connecting member fixed to each of the first and second members intermediate the first and second ends and extending between the first and second members. The first and second members are separated by the connecting member and one of the first and second members has a through channel arranged to be slidingly received on a tissue piercing deployment wire and a configuration alterable by the tissue piercing deployment wire that permits release of the fastener from the tissue piercing deployment wire.

The configuration of the one of the first and second members is alterable by being tearable by the tissue piercing deployment wire. The member may have a sidewall that is tearable by the tissue piercing deployment wire. The sidewall may have a varying thickness, such as by a scoring line, to assist in the sidewall tearing.

Alternatively, the configuration of the one of the first and second members may be alterable by being deformable by the tissue piercing deployment wire. The member may have a sidewall that is deformable by the tissue piercing deployment wire. The sidewall may include a lengthwise slit. The lengthwise slit may be continuous from the first end to the second end. The slit may include a slot portion.

The invention still further provides a fastener assembly for use in a mammalian body, comprising a fastener including a first member, a second member, the first and second members having first and second ends, and a connecting member fixed to each of the first and second members intermediate the first and second ends and extending between the first and second members. The first and second members are separated by the connecting member and one of the first and second members has a longitudinal axis and a through channel along the axis. The assembly further includes a deployment wire arranged to be slidingly received by the through channel of the one of the first and second members and to pierce into the tissue and a pusher that pushes the one of first and second members into the tissue while on the deployment wire. The one of the first and second members has a configuration that is alterable by the tissue piercing deployment wire that permits release of the fastener from the tissue piercing deployment wire upon relative movement of the one of the first and second members and the tissue piercing deployment wire.

The pusher is tubular having a distal end, a sidewall, a lumen, and an opening in the sidewall communicating with the lumen. The pusher is carried on the tissue piercing deployment wire, which extends through the sidewall opening, into the lumen, and beyond the distal end of the pusher. The one of the first and second members is carried on the deployment wire between the deployment wire end and the distal end of the pusher to be arranged to pierce into the tissue upon being pushed by the pusher.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify like elements, and wherein:

FIG. 11 is a perspective view with portions cut away of a fastener assembly according to a second embodiment of the invention in an early stage of deploying a further fastener embodiment of the invention;

FIG. 12 is a perspective view of the assembly of FIG. 11 shown with the fastener being driven in the tissue layers to be fastened;

DETAILED DESCRIPTION

Figure 1:
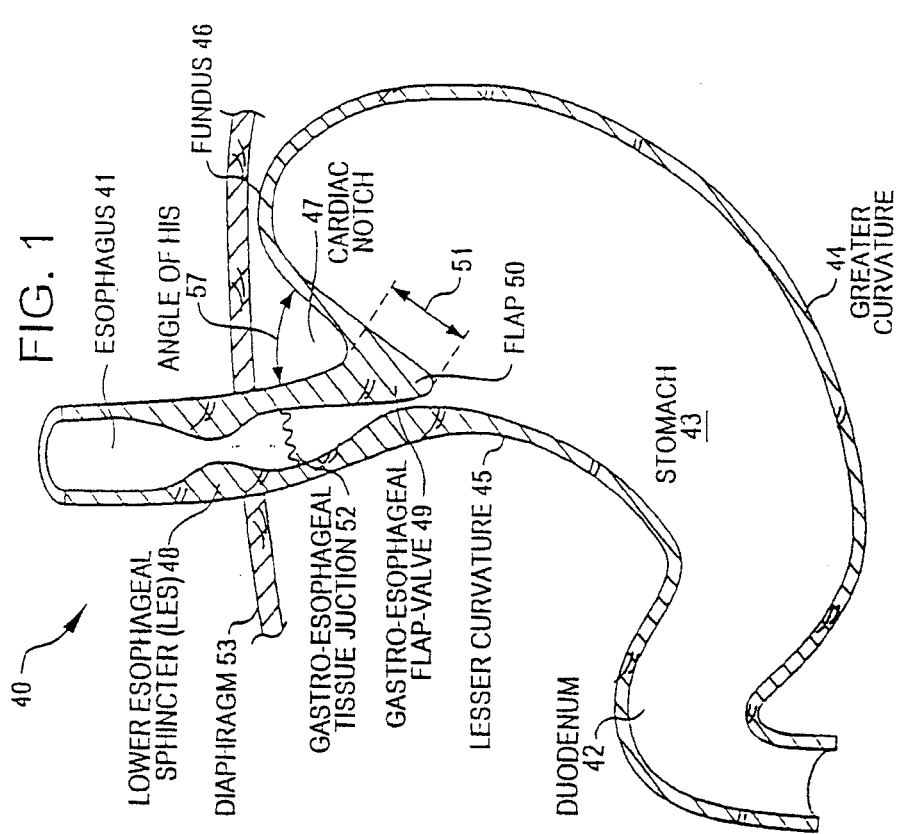
FIG. 1 is a front cross-sectional view of the esophageal-gastro-intestinal tract from a lower portion of the esophagus to the duodenum.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue. The fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion. The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43, is about 4 to 5 cm long (51) at it longest portion, and the length may taper at its anterior and posterior ends. The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

Figure 2:
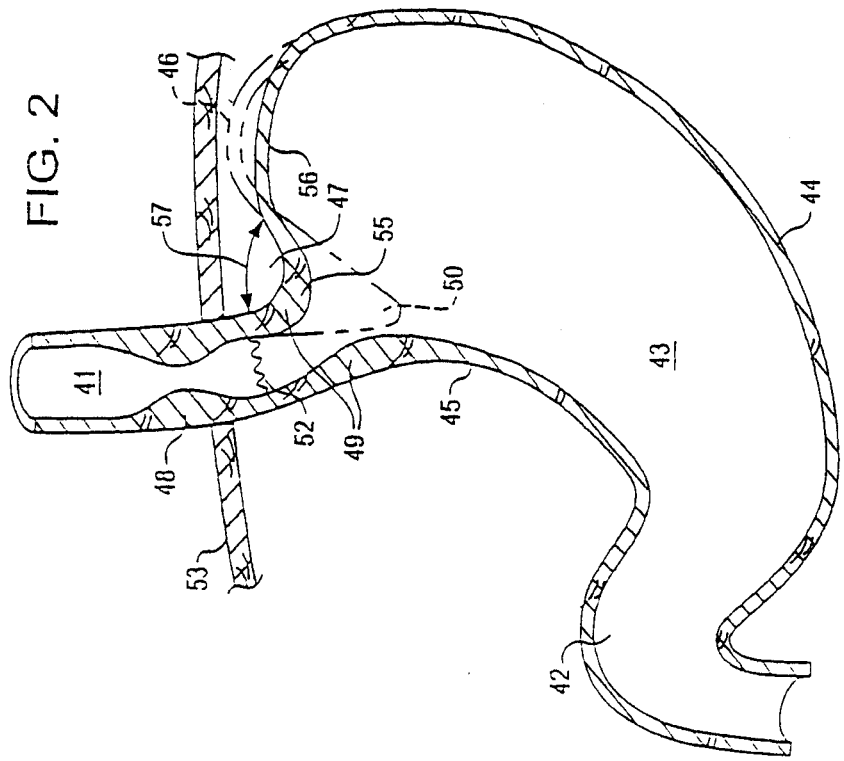
FIG. 2 is a front cross-sectional view of the esophageal-gastro-intestinal tract illustrating a Grade I normal appearance movable flap of the gastroesophageal flap valve (in dashed lines) and a Grade III reflux appearance gastroesophageal flap of the gastroesophageal flap valve (in solid lines)

FIG. 2 is a front cross-sectional view of an esophageal-gastro-intestinal tract illustrating a Grade I normal appearance movable flap 50 of the GEFV 49 (shown in dashed lines) and a deteriorated Grade III gastroesophageal flap 55 of the GEFV 49 (shown in solid lines). As previously mentioned, a principal reason for regurgitation associated with GERD is the mechanical failure of the deteriorated (or reflux appearance) gastroesophageal flap 55 of the GEFV 49 to close and seal against the higher pressure in the stomach. Due to reasons including lifestyle, a Grade I normal gastroesophageal flap 50 of the GEFV 49 may deteriorate into a Grade III deteriorated gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56. The deteriorated gastroesophageal flap 55 illustrates a gastroesophageal flap valve 49 and cardiac notch 47 that have both significantly degraded. Dr. Hill and colleagues developed a grading system to describe the appearance of the GEFV and the likelihood that a patient will experience chronic acid reflux. L. D. Hill, et al., The gastroesophageal flap valve: in vitro and in vivo observations, Gastrointestinal Endoscopy 1996:44:541-547. Under Dr. Hill's grading system, the normal movable flap 50 of the GEFV 49 illustrates a Grade I flap valve that is the least likely to experience reflux. The deteriorated gastroesophageal flap 55 of the GEFV 49 illustrates a Grade III (almost Grade IV) flap valve. A Grade IV flap valve is the most likely to experience reflux. Grades II and III reflect intermediate grades of deterioration and, as in the case of III, a high likelihood of experiencing reflux. With the deteriorated GEFV represented by deteriorated gastroesophageal flap 55 and the fundus 46 moved inferior, the stomach contents are presented a funnel-like opening directing the contents into the esophagus 41 and the greatest likelihood of experiencing reflux. Disclosed subsequently is a fastener and assembly, which may be employed to advantage in restoring the normal gastroesophageal flap valve anatomy.

Figure 3:
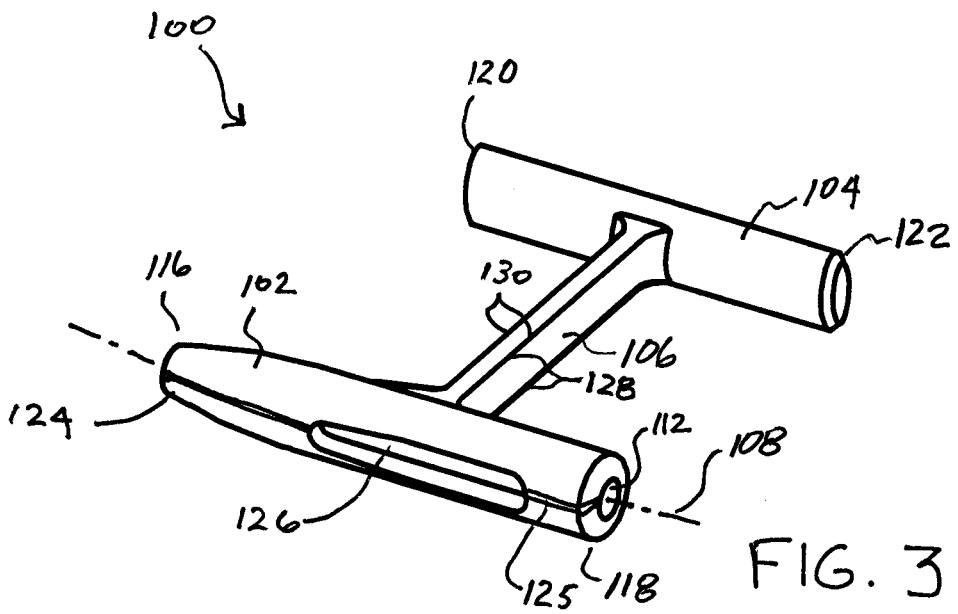
FIG. 3 is a perspective view of a fastener embodying the invention.
Figure 4:
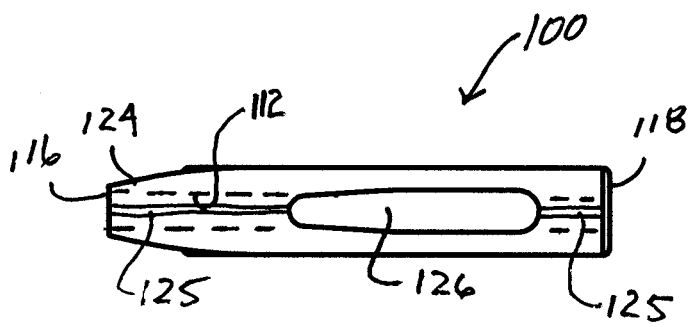
FIG. 4 is a side view of the fastener of FIG. 3.

FIG. 3 is a perspective view and FIG. 4 is a side view of a fastener 100 embodying the present invention. The fastener 100 generally includes a first member 102, a second member 104, and a connecting member 106. As may be noted in FIG. 3, the first member 102 and second member 104 are substantially parallel to each other and substantially perpendicular to the connecting member 106 which connects the first member 102 to the second member 104.

The first member 102 is generally cylindrical or can have any other shape. It has a longitudinal axis 108 and a through channel 112 along the longitudinal axis 108. The through channel 112 is formed by a through bore which is dimensioned to be slidingly received on a tissue piercing deployment wire to be described.

The first member 102 also includes a first end 116 and a second end 118. Similarly, the second member 104 includes a first end 120 and a second end 122. The first end 116 of member 102 forms a pointed dilation tip 124. The dilation tip 124 may be conical and more particularly takes the shape of a truncated cone. The tip can also be shaped to have a cutting edge in order to reduce tissue resistance.

The first and second members 102 and 104 and the connecting member 106 may be formed of different materials and have different textures. These materials may include, for example, plastic materials such as polypropylene, polyethylene, polyglycolic acid, polyurethane, or a thermoplastic elastomer. The plastic materials may include a pigment contrasting with body tissue color to enable better visualization of the fastener during its deployment. Alternatively, the fastener may be formed of a metal, such as stainless steel or a shape memory metal, such as Nitinol.

As may be further noted in FIG. 3, the connecting member 106 has a vertical dimension 128 and a horizontal dimension 130 which is transverse to the vertical dimension. The horizontal dimension is substantially less than the vertical dimension to render the connecting member 106 readily bendable in a horizontal plane. The connecting member is further rendered bendable by the nature of the material from which the fastener 100 is formed. The connecting member may be formed from either an elastic plastic or a permanently deformable plastic. An elastic material would prevent compression necrosis in some applications.

It may be noted in FIGS. 3 and 4, that the first member 102 has a continuous lengthwise slit 125 extending between the first and second ends 116 and 118. The slit 125 includes an optional slot portion 126 that communications with the through channel 112. The slot 126 has a transverse dimension for more readily enabling receipt of a tissue piercing deployment wire during deployment of the fastener 100. Also, because the fastener number 102 is formed of flexible material, the slit 125 may be made larger through separation to allow the deployment wire to be snapped into and released from the through channel 112 as will be seen subsequently. This permits early release of the first member during deployment 102 and decreases compression on the tissue layers.

The slit 125 extends substantially parallel to the through channel 112 and the center axis 108 of the first member 102. It may also be noted that the slit 125 has a width dimension that is smaller or less than the diameter D of the through channel 112. This assures that the fastener 100 will remain on a tissue piercing deployment wire as it is pushed towards and into the tissue as will be seen subsequently.

Figure 5:
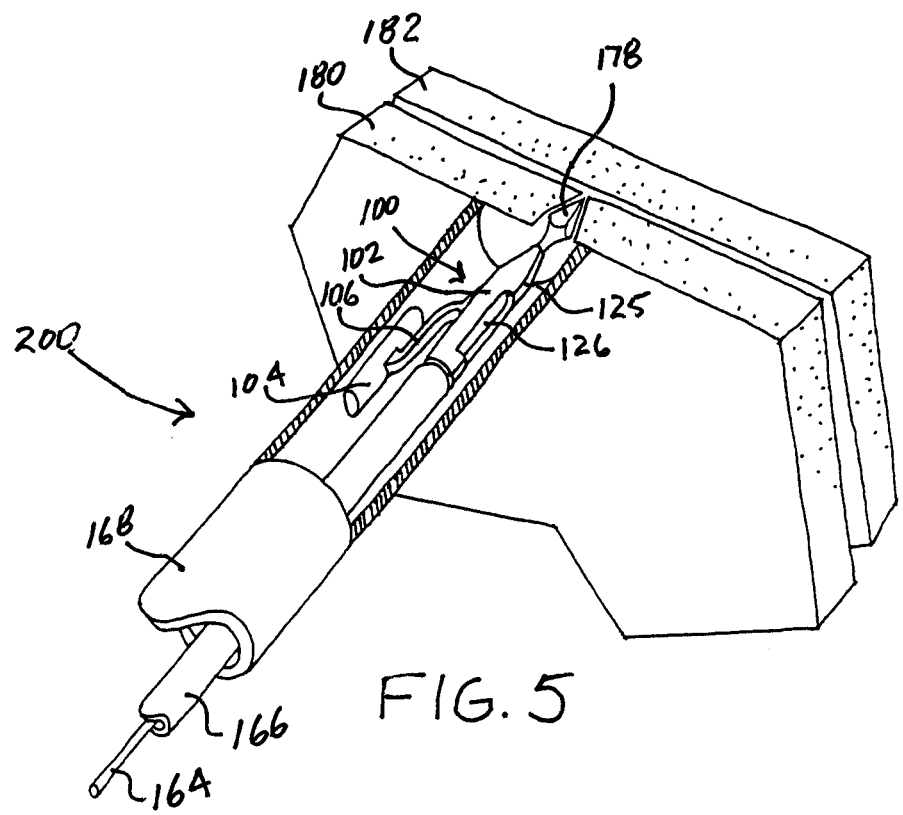
FIG. 5 is a perspective view with portions cut away of a fastener assembly according to a first embodiment of the invention in an early stage of deploying the fastener of FIGS. 3 and 4.

Referring now to FIG. 5, it is a perspective view with portions cut away of a fastener assembly 200 embodying the present invention for deploying the fastener 100. The tissue layer portions above the fastener 100 have been shown cut away in FIGS. 5-9 to enable the deployment procedure to be seen more clearly. The assembly 200 generally includes the fastener 100, a deployment wire 164, a pusher 166, and a guide tube 168.

The first member 102 of the fastener 100 is slidingly received on the deployment wire 164. The deployment wire 164 has a pointed tip 178 for piercing the tissue layers 180 and 182 to be fastened together. The tip 178 is enlarged with respect to the diameter of the deployment wire 164 and preferably has a cross-sectional dimension greater than that of the through channel and preferably the first member 102. This permits the tip 178 to cut sufficient tissue to enable the fastener member 102 to readily pass through the tissue layers 180 and 182. It may also serve as a guide to guide the wire 164 off of the member 102 at the end of the deployment. The tissue piercing wire 164, fastener 100, and the pusher 166 are all within the guide tube 168. The guide tube 168 may take the form of a catheter, for example, as previously mentioned, or a guide channel within a block of material.

As will be further noted in FIG. 5, the second member 104 is disposed along side the first member 102. This is rendered possible by the flexibility of the connecting member 106.

With the first member 102 of the fastener 100 slidingly received on the tissue piercing wire 164 and with the pusher 166 just touching the first member 102 on the tissue piercing wire 164, the tip 178 of the tissue piercing wire 164 pierces the tissue layers 180 and 182. The subassembly of the tissue piercing wire 164, fastener 100, and pusher 166 may be guided to its intended location relative to the tissue layers 180 and 182 by the guide tube 168.

Figure 6:
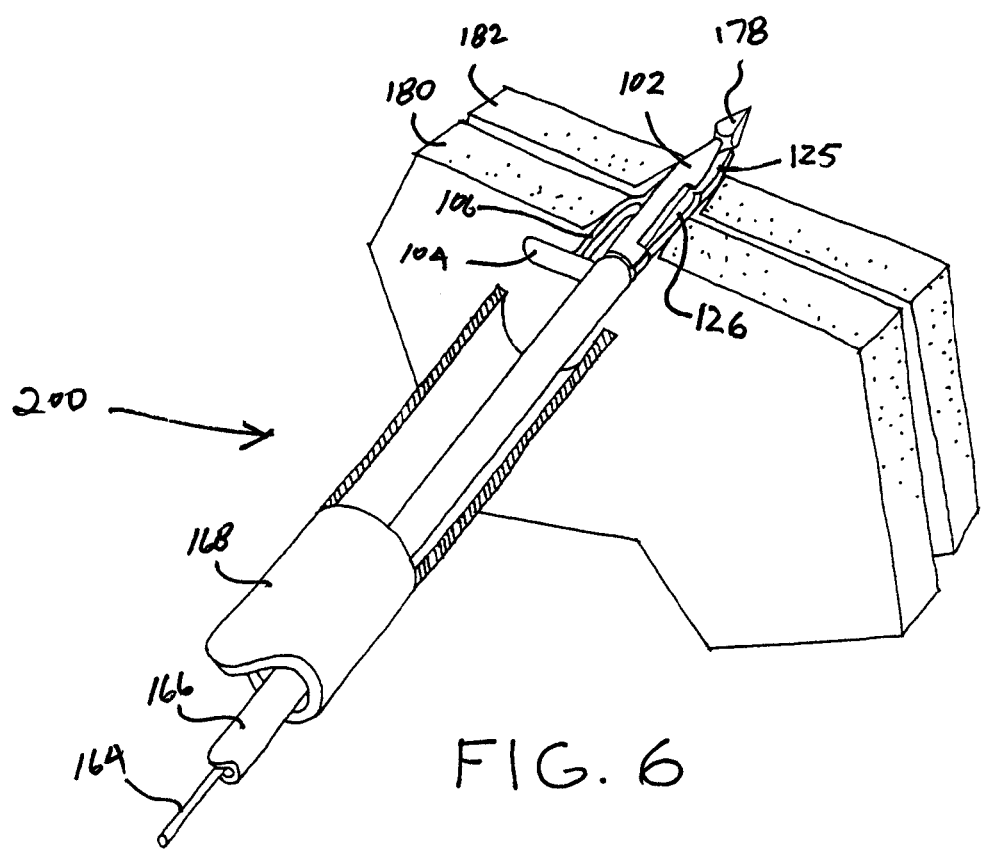
FIG. 6 is a perspective view of the assembly of FIG. 5 shown with the fastener being driven in the tissue layers to be fastened.

As shown in FIG. 6, the tissue piercing wire 164 has pierced the tissue layers 180 and 182 and the pusher 166 has pushed the first member 102 of the fastener 100 through the tissue layers 180 and 182 on the tissue piercing wire 164. This may be accomplished by moving the wire 164 and the pusher 166 together.

Figure 7:
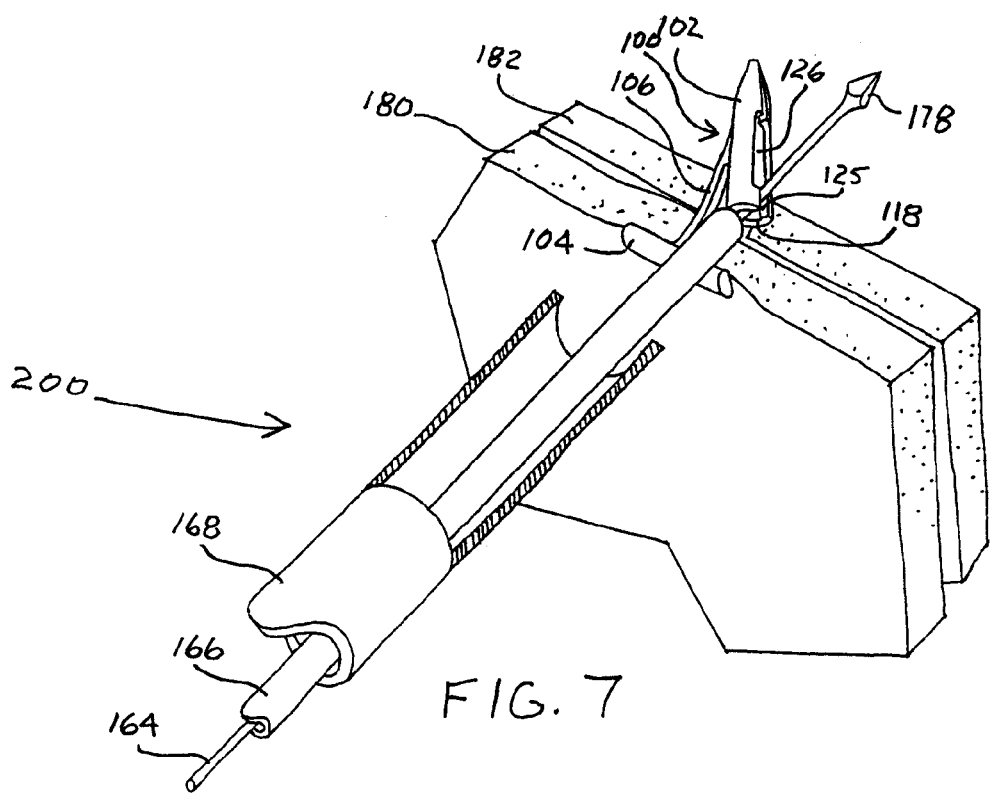
FIG. 7 is a perspective view of the assembly of FIG. 5 shown with the fastener in an intermediate stage of deployment.

As may be seen in FIG. 7, wire 164 has been pushed further forward and independently from the first member 102. The first member 102 has also been pushed forward by the pusher 166 to cause the second member 104 to engage the tissue layer 180. Continued pushing of the first member 102 causes the first member to pivot in a counter clockwise direction because the second member 104 is held by the tissue layer 180. The counter clockwise movement of the first member 102 causes the wire 164 to spread the slit 125 open, to pass down the slit to enter slot portion 126 and to eventually pass through the slit 125 at end 118. The fastener 100 is then released from the wire 164.

Figure 8:
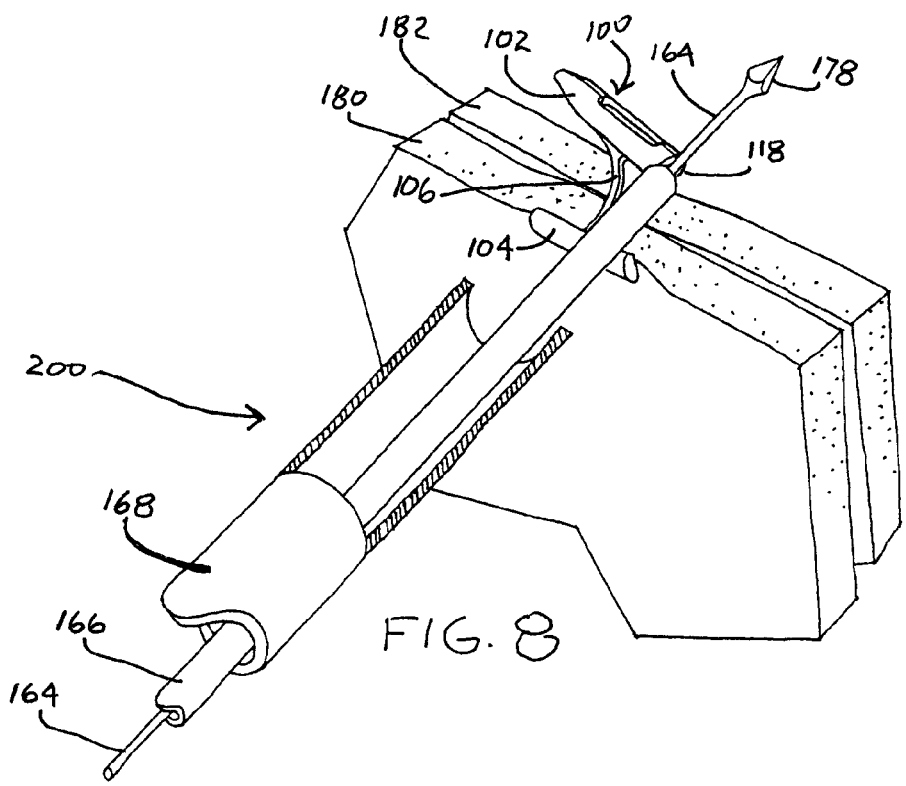
FIG. 8 is a perspective view of the assembly of FIG. 5 shown with the fastener almost completely deployed.

In FIG. 8, it will now be seen that the second end 118 of the first member 102 has cleared the wire 164 and tissue layer 182. The tissue piercing wire 164 may now be retracted into the pusher 166 and the tissue piercing wire 164 and pusher 166 may be withdrawn.

Figure 9:
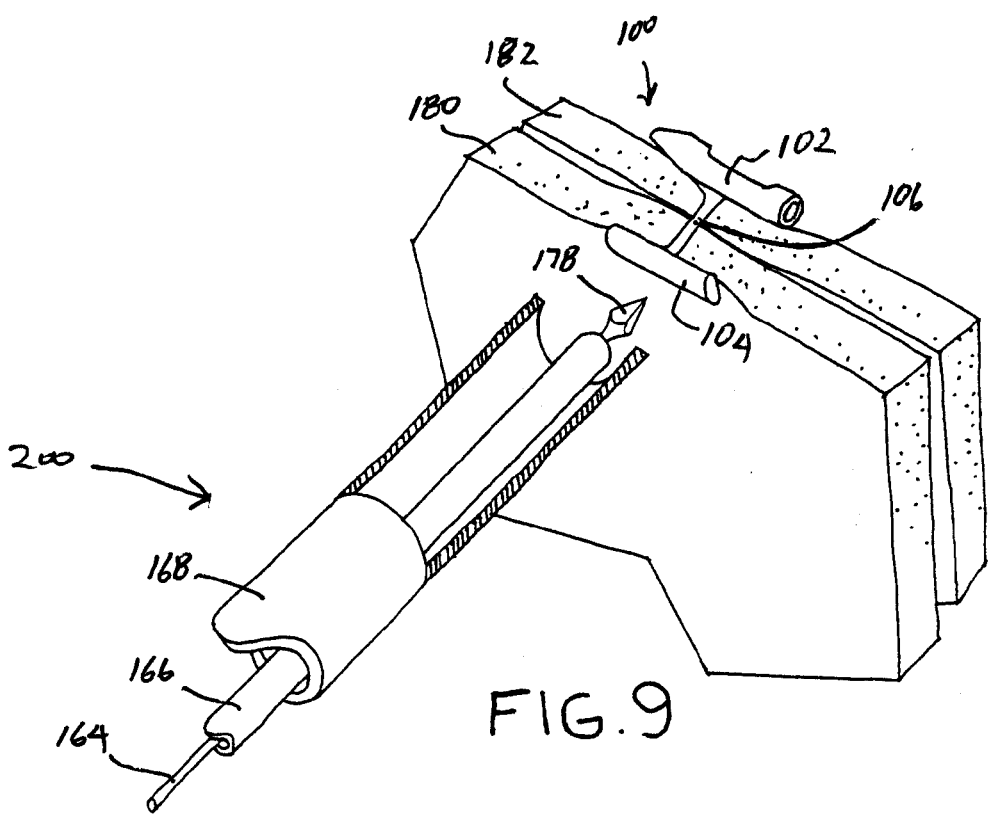
FIG. 9 is a perspective view showing the fastener of the assembly of FIG. 5 fully deployed and securely fastening a pair of tissue layers together.

FIG. 9 illustrates the fastener 100 in its fully deployed position. It will be noted that the fastener has returned to its original shape. The tissue layers 180 and 182 are fastened together between the first member 102 of the fastener 100 and the second member 104 of the fastener 100. The connecting member 106 extends through the tissue layers 180 and 182.

The release of the fastener 100 from the wire 164 with minimal damage to the tissue layers 180 and 182 is made possible because the first member 102 has a configuration alterable by the wire 164. The slit 125 in member 102 assists in the configuration change and release.

Figure 10:
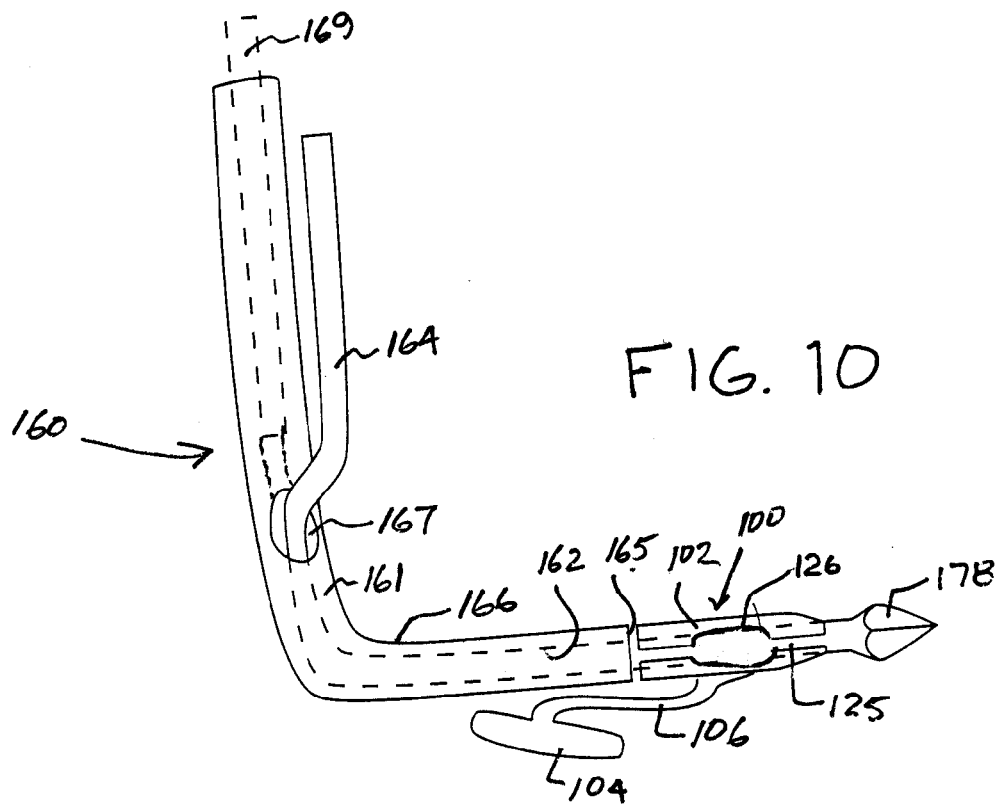
FIG. 10 is an exploded side view of a deployment wire and pusher arrangement according to an embodiment of the invention.
Figure 13:
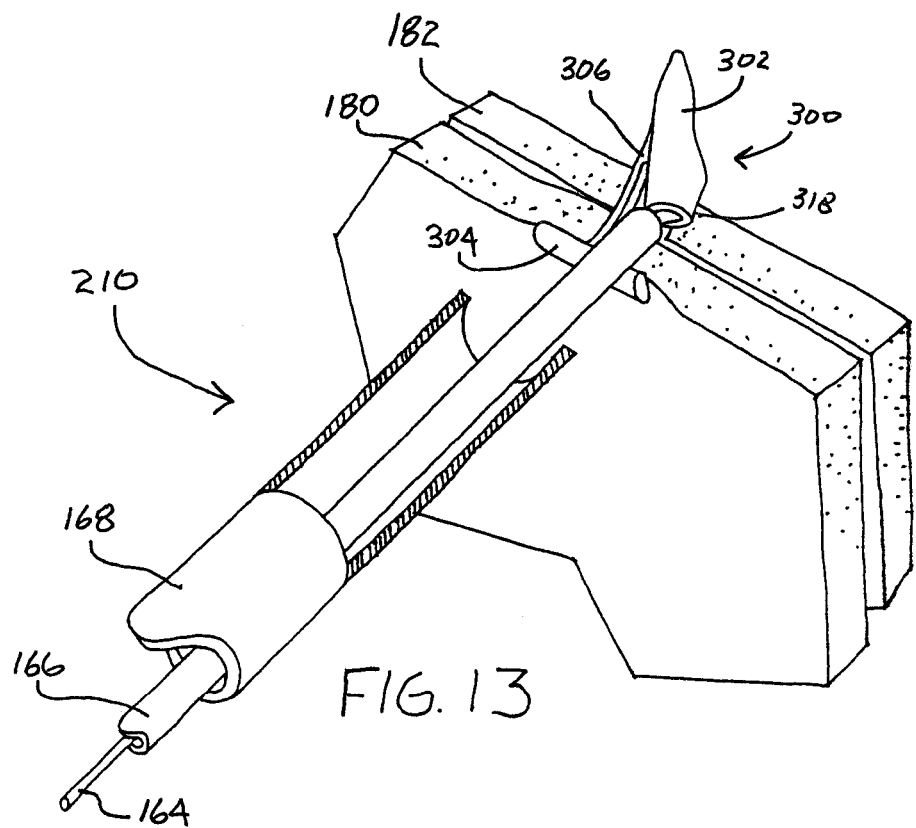
FIG. 13 is a perspective view of the assembly of FIG. 11 shown with the fastener in an intermediate stage of deployment.
Figure 14:
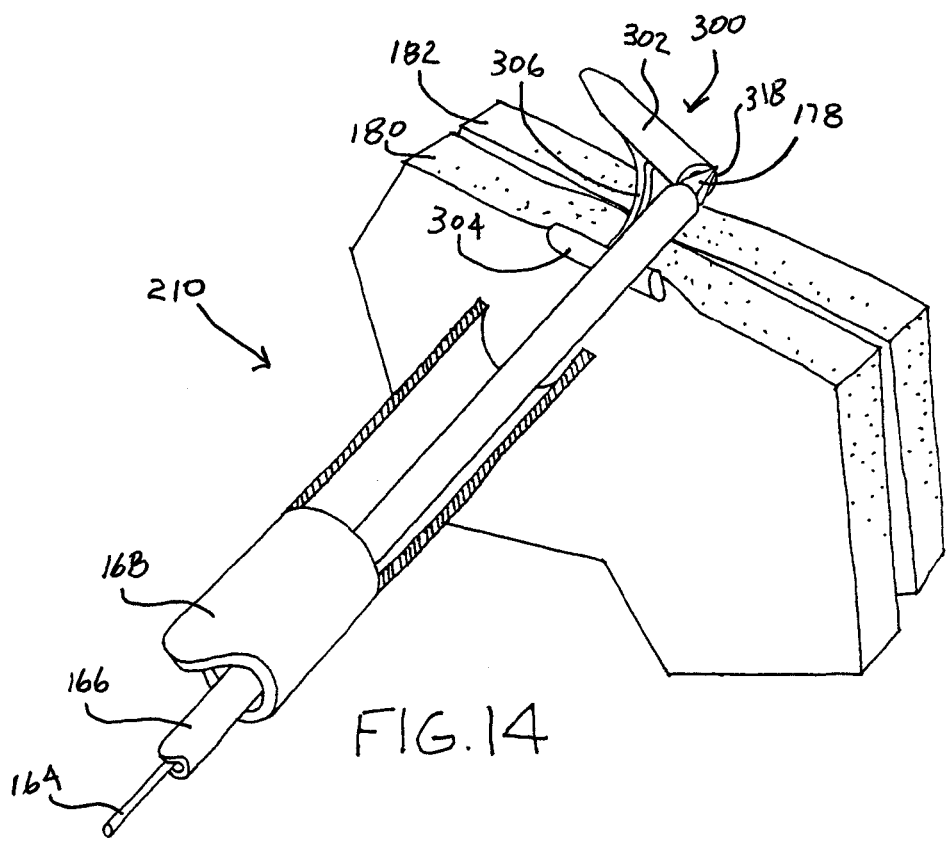
FIG. 14 is a perspective view of the assembly of FIG. 11 shown with the fastener almost completely deployed.

Referring now to FIG. 10, it shows a deployment wire/pusher arrangement 160 which may be employed in the assembly 200 of FIGS. 5-9. The arrangement 160 includes the deployment piercing wire 164 and the pusher 166. The wire 164 includes the tissue piercing tip 178. The pusher 166 is tubular and has a distal end 165, a lumen 162, and an opening 167 through the pusher sidewall 161 and communicating with the lumen 162. The lumen 162 is configured to permit the pusher 166 to slidingly be carried on the wire 164. To that end, the wire extends within the lumen 162 from the distal end 165 and through the opening 167. A fastener 100, of the type previously described, has been snapped onto the deployment wire 164 between the deployment wire tip 178 and the distal end 165 of the pusher 166. An optional stiffener 169 may also be provided for the pusher 166.

After a fastener is deployed, the pusher 166 may be retracted from the patient while the pusher is still on the deployment wire 164, a further fastener may then be snapped onto the wire through the slit 125. The pusher may then be advanced down the deployment wire to deploy the fastener as previously described.

FIGS. 11-15 show a deployment sequence of another fastener assembly 210 embodying the invention. As shown in FIG. 11, the assembly 210 includes the deployment wire 164, the pusher 166, the guide tube 168, and a fastener 300. The fastener 300 includes a first member 302, a second member 304, and a connecting member 306. The fastener 300 is similar to the fastener 100 previously described except that to render the configuration of the first member 302 alterable by the deployment wire 164 as the first member 102 is so alterable, the first member 302 is stretchable to obviate the need for a slit. More specifically, the first member 302 may be formed of rubber, for example, to permit the wire 164 to be separated from the member 302 by simply pulling the wire tip 178 back through through the member. Deformation of the member 302 occurs to permit this separation.

FIG. 11 shows the fastener 300 on the wire with the wire tip 178 just piercing the tissue layer. The first member 302 is carried on the wire 164 which extends through the through channel of the first member 302.

As seen in FIG. 12, the pusher 166 and wire 164 are moved forward together to cause the wire 164 and member 302 to extend through the tissue layers 180 and 186. From this point, as may be seen in FIG. 13, the pusher pushes the member 302 forward. The second member 304 first engages tissue layer 180 and once so engaged, the first member 302 is caused to rotate (counter clockwise in FIG. 13). The elasticity of the member 302 causes the wire tip to stretch the sidewall of the first member 302. As the member 302 is continued to be pushed, and with optional retraction of the deployment wire 114, it continues to rotate. Eventually, the end 318 of the member 302 pops free of the wire tip. This may be seen in FIG. 14. The end 318 of the member is now free of the wire 164.

Figure 15:
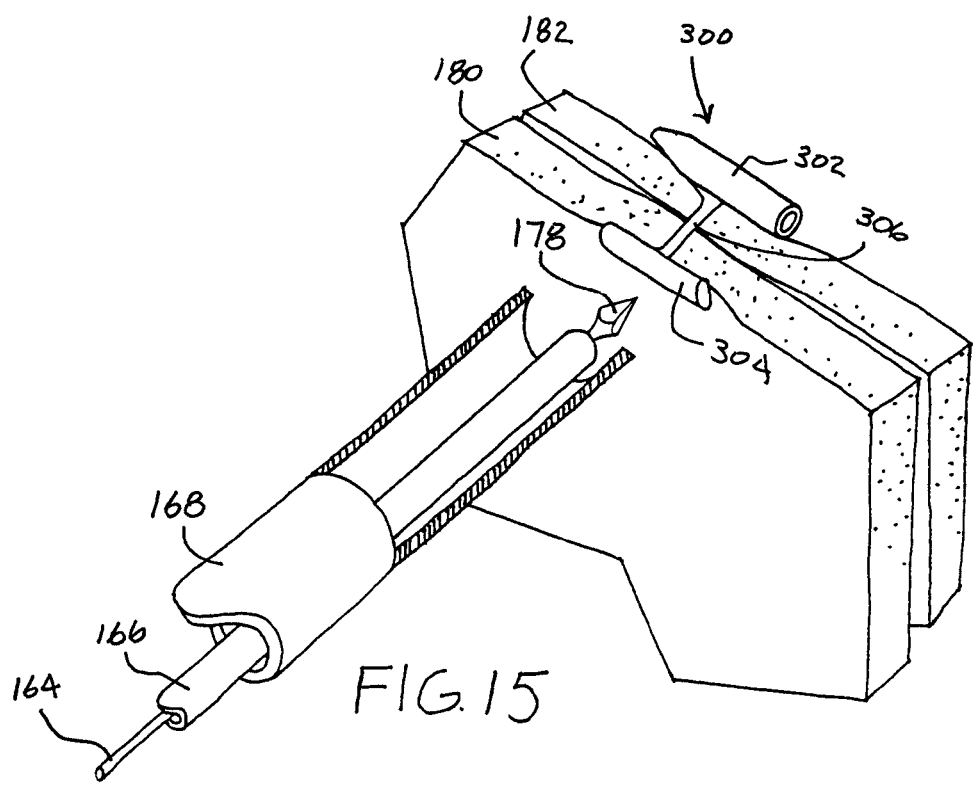
FIG. 15 is a perspective view showing the fastener of the assembly of FIG. 11 fully deployed and securely fastening a pair of tissue layers together.

The pusher 166 and deployment wire 164 may now be extracted. As shown in FIG. 15, the tissue layers 180 and 182 are now fixed together between the first and second members 302 and 304 with the connecting member 306 extending therebetween.

Figure 16:
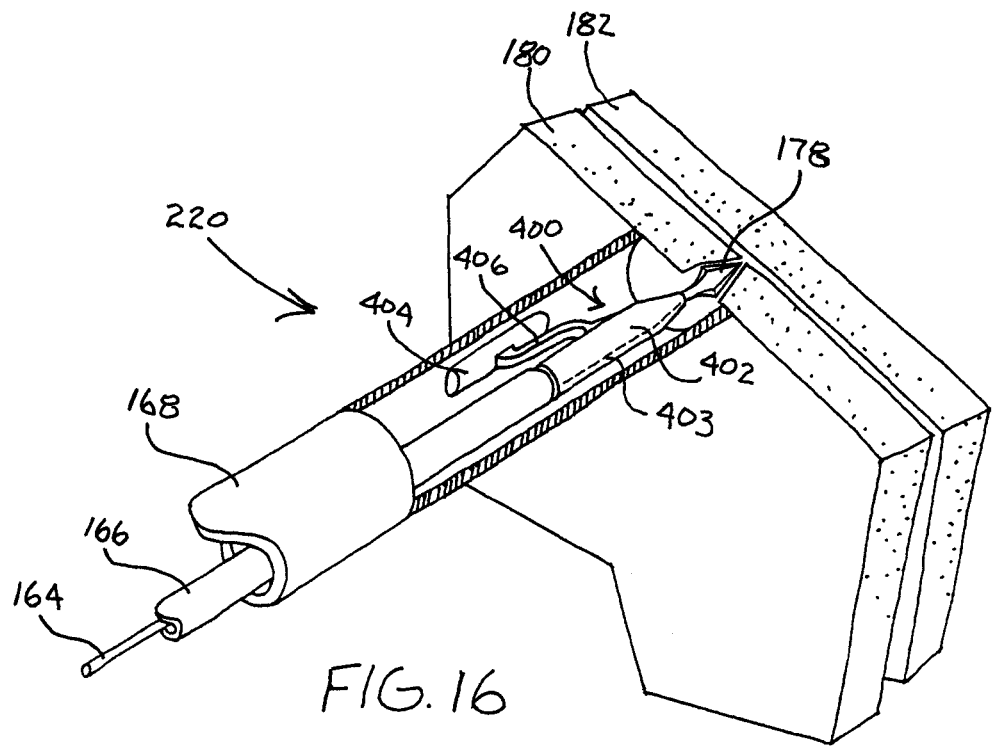
FIG. 16 is a perspective view with portions cut away of a fastener assembly according to a still further embodiment of the invention in an early stage of deploying a still further fastener embodiment of the invention.

FIGS. 16-20 show a deployment sequence of another fastener assembly 220 embodying the invention. As shown in FIG. 16, the assembly 220 includes the deployment wire 164, the pusher 166, the guide tube 168, and a fastener 400. The fastener 400 includes a first member 402, a second member 404, and a connecting member 406. The fastener 400 is similar to the fasteners 100 and 300 previously described except that, to render the configuration of the first member 402 alterable by the deployment wire 164, the first member 402 is tearable by tip 178 of the wire 164. More specifically, the first member 402 may be formed, for example, to permit the wire 164 to tear the member 402 lengthwise as the wire tip 178 is pulled back through through the member 402. To assist the tearing, the member sidewall may have a varying thickness, such as a tearing or score line 403.

FIG. 16 shows the fastener 400 on the wire with the wire tip 178 just piercing the tissue layer. The first member 402 is carried on the wire 164 which extends through the through channel of the first member 402.

Figure 17:
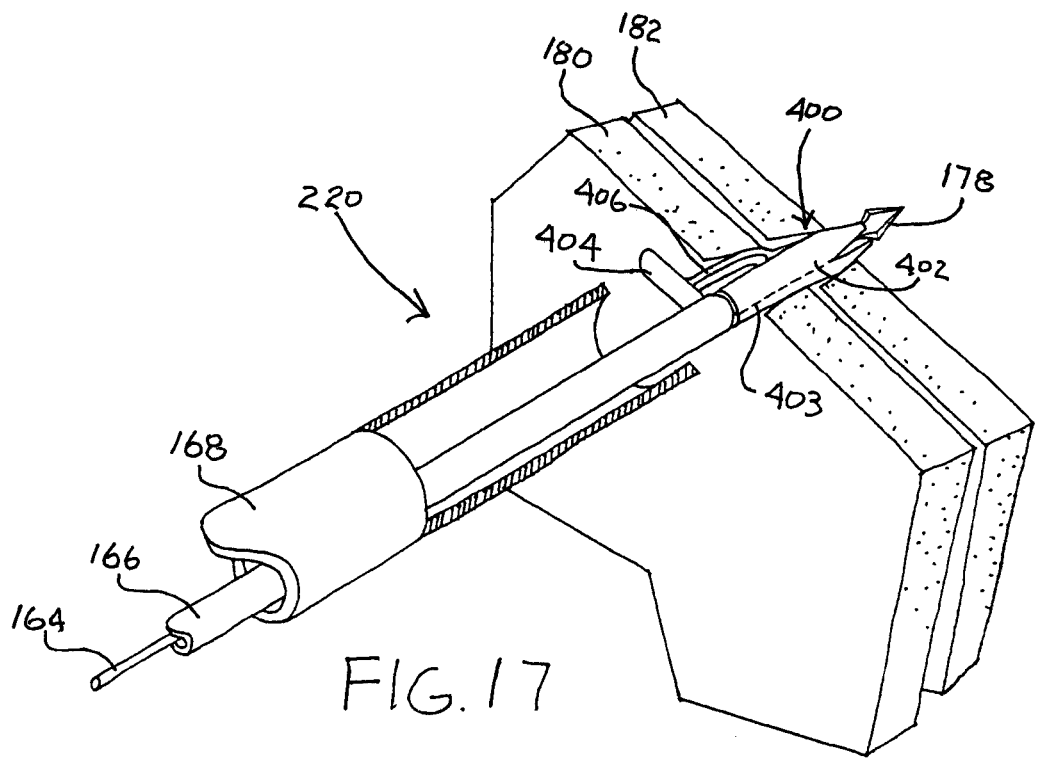
FIG. 17 is a perspective view of the assembly of FIG. 16 shown with the fastener being driven in the tissue layers to be fastened.
Figure 18:
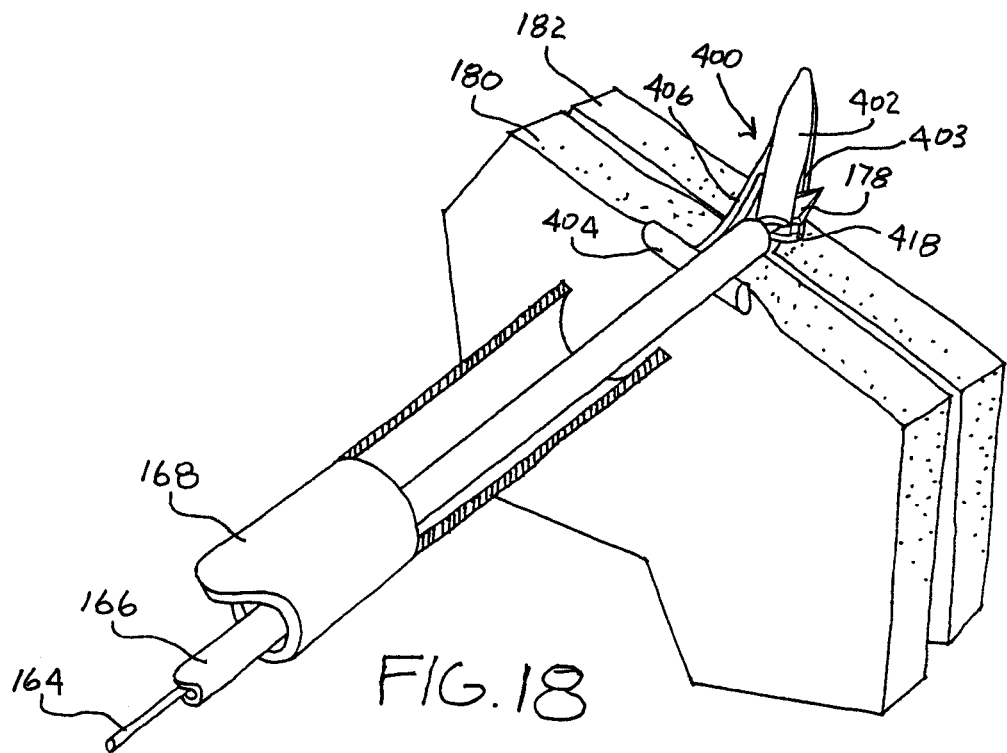
FIG. 18 is a perspective view of the assembly of FIG. 16 shown with the fastener in an intermediate stage of deployment.
Figure 19:
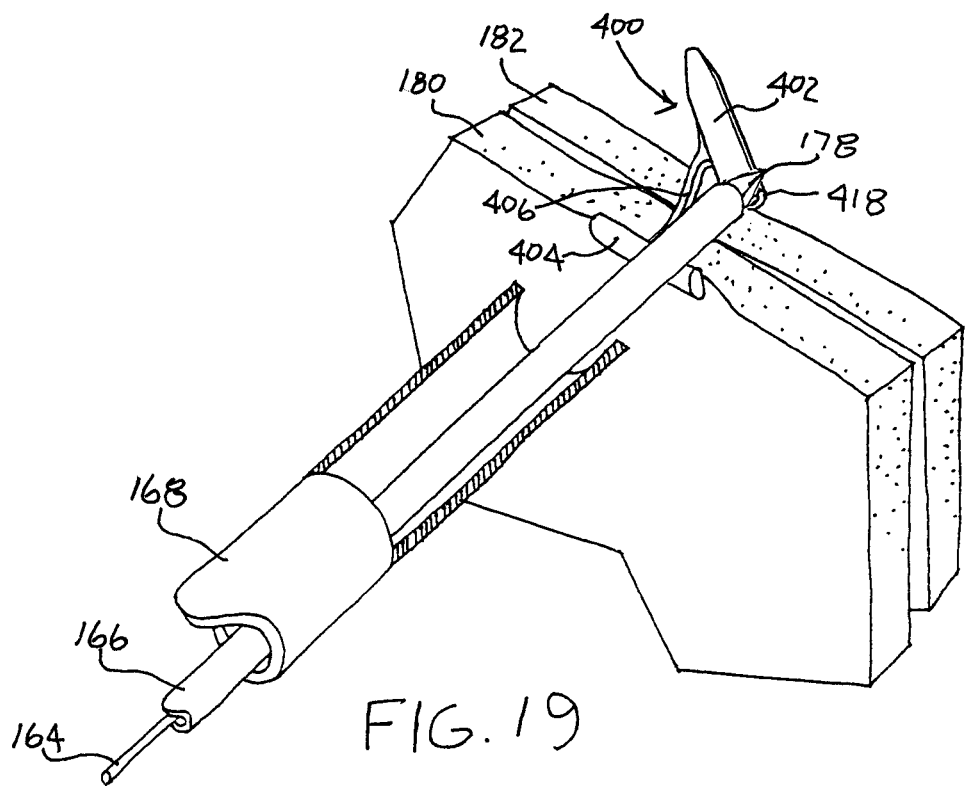
FIG. 19 is a perspective view of the assembly of FIG. 16 shown with the fastener almost completely deployed.

As seen in FIG. 17, the pusher 166 and wire 164 are moved forward together to cause the wire 164 and member 402 to extend through the tissue layers 180 and 186. From this point, the pusher 166 pushes the member 402 to cause the tip 178 to begin tearing the member 402 along the score line 402. As may be seen in FIG. 18, the pusher pushes the member 402 forward. The second member 404 first engages tissue layer 180 and once so engaged, the first member 402 is caused to rotate (counter clockwise in FIG. 18). The turning of the member 402 causes the wire tip 178 to tear through the sidewall of the first member 402. As the member 402 is continued to be pushed, it continues to be turned lengthwise. Eventually, the end 418 of the member 402 releases from the wire tip. This may be seen in FIG. 19. The end 418 of the member is now free of the wire 164.

Figure 20:
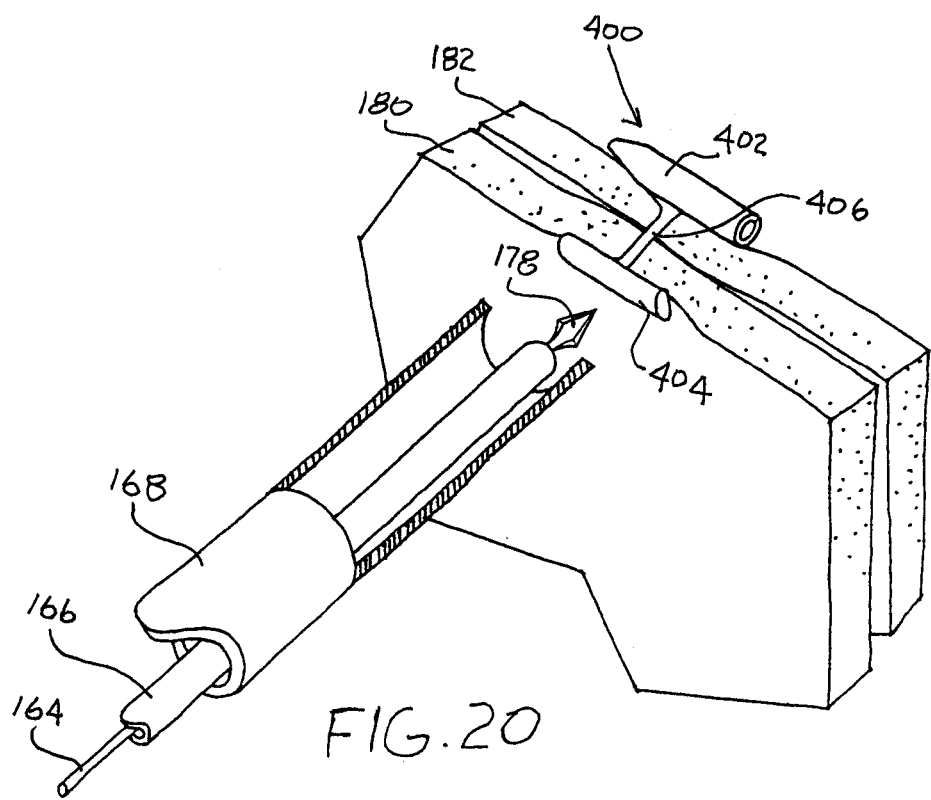
FIG. 20 is a perspective view showing the fastener of the assembly of FIG. 16 fully deployed and securely fastening a pair of tissue layers together.

The pusher 166 and deployment wire 164 may now be extracted. As shown in FIG. 20, the tissue layers 180 and 182 are now fixed together between the first and second members 402 and 404 with the connecting member 406 extending therebetween.

While the invention has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. A method for fastening tissue in a mammalian body, comprising:

providing a fastener and a deployment wire, the fastener including a first member and a second member connected to the first member, only the first member having a through channel dimensioned to be slidingly received on the deployment wire and a slit configured to be made larger so that the deployment wire can be snapped onto and released from the through channel;

snapping the deployment wire through the slit and into the through channel;

advancing a pusher over the deployment wire, the deployment wire extending through a sidewall opening of the pusher, into a pusher lumen, and beyond a distal end of the pusher;

advancing the fastener over the deployment wire using the pusher;

wherein only the first member of the fastener advances over the deployment wire between a deployment wire end and the distal end of the pusher; and a distal end of the first member configured to pierce into the tissue upon being pushed by the pusher.

2. The method for fastening tissue of claim 1, wherein the first member includes the distal end and a proximal end, the slit extending between the distal and proximal ends and communicating with the through channel, further comprising expanding the slit so that the deployment wire can be snapped into the through channel.

3. The method for fastening tissue of claim 2, wherein a guide tube extends over the deployment wire and the fastener, the second member being disposed next to the first member within the guide tube.

4. The method for fastening tissue of claim 3, arranging the first and second members side by side when the first member is slidingly received on the deployment wire.

5. The method for fastening tissue of claim 4, advancing the pusher distally over the deployment wire thereby pushing the fastener into contact with tissue.

6. The method for fastening tissue of claim 5, advancing the deployment wire through the guide tube so that a piercing tip of the deployment wire advances through two tissue layers.

7. The method for fastening tissue of claim 6, further advancing the pusher over the deployment wire thereby pushing the first member of the fastener over the deployment wire and through the two tissue layers.

8. The method for fastening tissue of claim 7, continued pushing of the first member by the pusher causes the first member to pivot counter clockwise because the second member abuts, but does not penetrate, the two tissue layers.

9. The method for fastening tissue of claim 8, the counter clockwise rotation of the first member causes the deployment wire to spread open the slit in the first member so that the fastener is released from the deployment wire.

10. The method for fastening tissue of claim 9, retracting the deployment wire and pusher in the guide tube.

* * * * *